United States Patent [19]

Kraemer et al.

[11] 4,388,271
[45] Jun. 14, 1983

[54] RAPID DIAGNOSTIC AGENTS

[75] Inventors: Dieter Kraemer, Mainz; Klaus Lehmann, Rossdorf; Roland Hartl, Muenster, all of Fed. Rep. of Germany

[73] Assignee: Röhm GmbH, Darmstadt, Fed. Rep. of Germany

[21] Appl. No.: 300,899

[22] Filed: Sep. 10, 1981

Related U.S. Application Data

[63] Continuation-in-part of Ser. No. 110,905, Jan. 10, 1980, abandoned.

[51] Int. Cl.³ ............................................. G01N 33/72
[52] U.S. Cl. ...................... 422/56; 436/66; 436/904
[58] Field of Search ............... 23/230 B, 931, 932; 252/408; 422/56–58; 436/66, 904

[56] References Cited

U.S. PATENT DOCUMENTS

| | | | |
|---|---|---|---|
| 2,229,155 | 1/1941 | Wenker | 422/56 |
| 3,061,523 | 10/1962 | Free | 435/14 |
| 3,212,855 | 10/1965 | Mast et al. | 23/253 |
| 3,552,929 | 1/1971 | Fields et al. | 23/230 B X |
| 3,630,957 | 12/1971 | Rey et al. | 435/28 X |
| 3,846,247 | 11/1974 | Kronish et al. | 422/56 X |
| 3,853,472 | 12/1974 | Rittersdorf et al. | 23/253 |
| 3,996,006 | 12/1976 | Pagano | 23/253 |
| 4,017,261 | 4/1977 | Svoboda et al. | 23/253 |
| 4,038,485 | 7/1977 | Johnston et al. | 23/230 |
| 4,225,557 | 9/1980 | Hartl et al. | 23/253 |
| 4,283,491 | 8/1981 | Dappen | 422/56 X |

FOREIGN PATENT DOCUMENTS 2460903 6/1976 Fed. Rep. of Germany.
2652545 5/1977 Fed. Rep. of Germany.
2004062 3/1979 United Kingdom.

Primary Examiner—Arnold Turk
Attorney, Agent, or Firm—Curtis, Morris & Safford

[57] ABSTRACT

The invention relates to diagnostic agents for the rapid diagnostic detection of blood in excretions and body fluids, consisting essentially of a solid support which is charged with a chromogenic substance as indicator and impregnated with an acrylic and/or methacrylic resin.

5 Claims, 1 Drawing Figure

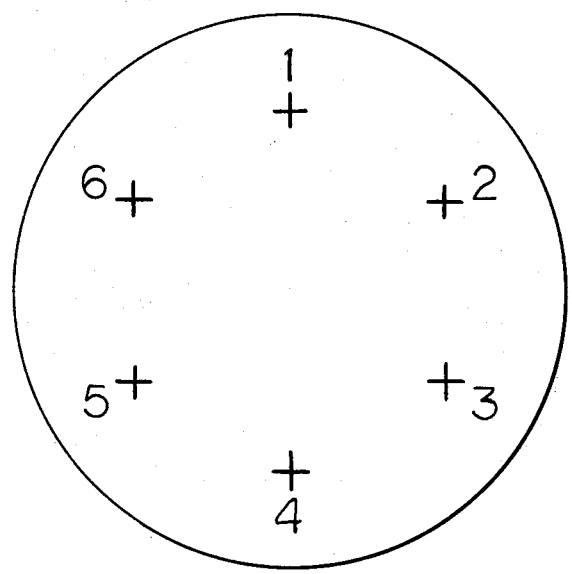

RAPID DIAGNOSTIC AGENTS

This is a continuation-in-part of application Ser. No. 110,905 filed Jan. 10, 1980 and now abandoned.

The need for simple, rapid and nevertheless reliable diagnostic methods has led in medicine to the development, inter alia, of the test-strip method.

The basic idea is to apply to a solid support a reagent which, after moistening and contact with the substance or substances to be detected, reacts directly or indirectly with a visually recognizable change, as a rule with the formation of a coloring substance or a change of color.

The test strips developed for the detection of the presence of blood in excretions such as stools or urine and in body fluids have acquired great practical importance. The test is based on the detection of hemoglobin, the peroxidase-active component of blood. In the presence of peroxide, a recognizable coloring or change of color occurs when hemoglobin reacts with any of a number of suitable indicators (chromogens). Suitable chromogens include guaiac and phenylamino compounds such as, for instance, o-toluidine, m-toluidine, the acid addition salts thereof, benzidine, 3,3',5,5'-tetramethyl benzidine, diphenylamine, 4-diphenyl sulfonic acid and 2,6-dichloroindophenol sodium.

The simultaneous use of certain thiazole compounds as sensitizers for the chromogens is recommended in German Offenlegungsschrift No. 26 52 545.

Detection of blood in the stool or in the urine requires a suitable support, such as for instance a strip of filter paper, which is impregnated with a chromogen, and to which a sample of the stool or urine to be examined is applied. "Development" is then effected, for instance by the addition of peroxide solution. For the construction of the test strip in detail various solutions have been proposed; for example, a multi-hole test strip is described in U.S. Pat. No. 3,996,006.

Practical experience has shown that it is critically important that a test strip method for detecting blood in the stool must be neither too sensitive nor too insensitive. If it is too sensitive, it will falsely indicate positive results, with attendant undesirable psychological and financial consequences. If the method is too insensitive, it will falsely indicate negative results.

It is particularly disturbing if the chromogen, even without action of the peroxidase-active hemoglobin, shows color change of a type which is similar to or the same as that which is indicated in qualitative tests for hemoglobin. Such disturbances are known when using indicator coloring substances (chromogens) from the above-mentioned class of the phenylamino compounds. Furthermore, an undesirably rapid fading of the intensity of the color until it is entirely gone is frequently observed in the case of certain representatives of this class of chromogens. As a whole therefore these indicator color substances, which are in themselves readily available in sufficient purity, can only be recommended very conditionally as chromogens for the detection of blood in the stool or urine.

It has now been found that the suitability of the indicators used as chromogens in the test for blood in excretions and body fluids, i.e. the suitability both of the guaiac coloring substance and of the corresponding phenylamino compounds which can be used, can be definitely improved if the support material for the chromogen—as a rule filter paper—is treated with a resin dispersion or solution, particularly with an aqueous (meth)-acrylic resin dispersion.

The prior art has proposed polymer coatings for diagnostic agents such as test strips which contain sensitive chromogens or enzymes. If protection of these sensitive materials against impairment by exposure to air and moisture is intended, then the production of a closed protective polymer film in or on the test strip appears to be the correct measure to be taken. Further, the use of polymers in the aforementioned diagnostic agents is based on the concept that the chromogen, statistically distributed in the diagnostic agent, is to be fixed to the carrier with the aid of the polymer in order to prevent mobility of "bleeding out" of the chromogen when the test strip is immersed in the liquid to be analyzed. This consideration—that the chromogen should be locally fixed on the diagnostic agent with the aid of a polymer—more or less excludes the use of a polymer to achieve the object of the present invention.

That is, the diagnostic agents according to the present invention have the bringing into play of a "chromatographic effect" as a prerequisite to achieving a necessary statistical reliability. As is known from U.S. Pat. No. 4,225,557, when the diagnostic agents claimed therein are used, the color formed in a positive test is transported by the developing agent to the periphery of the test site by the circularly spreading developer which is applied to the diagnostic agent to develop the color. This "concentration" of the colored material on the periphery of the test site which occurs as a result of the chromatographic effect is an unalterable requirement for the functioning of the diagnostic agent as a statistically reliable indicator. A fixation of the chromogen molecules onto the carrier material with a polymer—as intended in the prior art—would, however, interfere with or make impossible such a "chromatographic effect" involving peripheral concentration of the developed chromogen.

Thus, an impregnation of the diagnostic test strips which are contemplated according to the present invention with a polymer would be expected by one skilled in the art, from a knowledge of the prior art and the operation of the test strips, to cause the tests as known to fail, that is, to have a negative effect on their sensitivity. It must be considered surprising and unexpected that, quite to the contrary, an increased sensitivity of the diagnostic agents in the presence of an impregnating polymer is observed.

The phenylamino compounds which can be used as chromogens fall in general under the formula

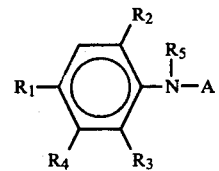

in which $R_1$ is a hydrophilic radical such as an OM or an $SO_3M$ group in which M stands for hydrogen or a metal cation, or $R_1$ is hydrogen or

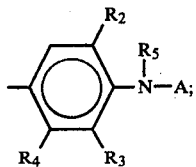

$R_2$, $R_3$ and $R_4$ independently of each other are hydrogen or lower alkyl, preferably methyl;

$R_5$ is hydrogen or, together with A and the nitrogen with which they are linked, a quinonimine; and A is hydrogen or a radical

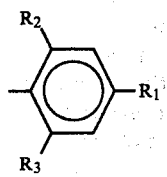

with the priviso that at least two phenyl radicals are present in the molecule and the sum of the numerical values of the subscripts of $R_1$, $R_2$, $R_3$ and $R_4$ on any one phenyl radical does not exceed a value of 6.

However, other chromogens may also be used for the process of the invention. Mention may be made of o-toluidine and m-toluidine as well as their acid addition salts, benzidine, 3,3',5,5'-tetramethylbenzidine, diphenylamine, 4-diphenyl sulfonic acid and its salts, and sodium 2,6-dichloroindophenol.

Guaiac is particularly important for the method of the invention. This is a resin from the guaiac trees (*Guajacum officinale L.* and *Guajacum sanctum L.*), trees which are frequently present in South and Central America. Information as to *lignum Guajaci* and the obtaining of guaiac in different qualities can be obtained from "Hagers Handbuch der pharmazeutischen Praxis" (Hagers Manual of Pharmaceutical Practice), Volume 1, 2nd revised edition, Springer Verlag (Berlin, Gottingen, Heidelberg) 1949, pages 1397 et seq.

In general the quality described there as *resina guajaci depurata* is suitable for the preparation of paper strips for the testing of blood in stool or urine, but it is possible via chromatography to obtain therefrom resinous substances which have the chromogenic action and which are suitable, individually or collectively, for the impregnating of test paper.

In practice the solubility of the chromogen, particularly the solubility thereof in water, is determinative of the method of application.

With water-soluble chromogens, the method of the invention can be suitably carried out by mixing the aqueous (meth)-acrylic resin dispersion, possibly in dilution, together with the chromogen, particularly those of the above formula, and uniformly or homogeneously impregnating the support, in particular filter paper, simultaneously with chromogen and resin by application thereto of the aqueous mixture thus obtained.

Water-insoluble chromogens such as guaiac are dissolved in suitable organic solvents and the paper is uniformly or homogeneously impregnated therewith. It can then be treated with an aqueous dispersion of (meth)-acrylic resin. The reverse sequence of steps is also possible. Further, the synthetic polymer in dry form can also be dissolved with the chromogen in the organic solvent and the two applied simultaneously to the paper uniformly or homogeneously to impregnate it.

A simultaneous application of the resin and chromogen is preferred.

In this connection the experience of the prior art can be adopted with respect to the selection of the support, particularly the filter paper, and the concentration and manner of application of the coloring-substance indicators.

As a guide, the concentration of the (meth)-acrylic resin dispersion in the aqueous medium intended for the impregnation may be of the order of about 1 to 10% by weight, preferably up to 5% by weight, and particularly about 3% by weight. Dilution of the original aqueous (meth)-acrylic resin dispersion, for instance of the commercial forms, may also be effected with the addition of a suitable organic diluent, e.g., ethanol.

The decisive factor for the success of the method is that the support be impregnated with a sufficient amount of the chromogen per unit of area or volume of the support. The quantities required for each individual chromogen can be considered to be substantially known.

As a guide, it is generally desirable to add to the filter paper about 0.1 to 10 mg of (meth)-acrylic resin/cm$^2$ of filter paper surface. When the resin is in the form of the particularly preferred dispersion of methacrylic acid/ethylacrylate in a ratio of 1:1 with a molecular weight of about 250,000, concentrations of between about 0.2 and 0.8 mg of resin/cm$^2$ of area, preferably about 0.3 mg of resin/cm$^2$ of area, are advantageous.

The concentration of the chromogens is advantageously such that between about 0.001 and 10 mg of the indicator coloring substance are present on 1 cm$^2$ of the surface of the support, depending on the data of the individual coloring substance. Thus it is calculated, for instance, that for the impregnation of 1 cm$^2$ of filter paper of a test strip there should be used 0.2 to 200 $\mu$g, preferably 1 to 10 $\mu$g, of o-toluidine or m-toluidine, or a corresponding amount of their acid addition salts, 1 to 100 $\mu$g and preferably 10 $\mu$g of benzidine, 1 to 200 $\mu$g and preferably 20 $\mu$g of 3,3',5,5'-tetramethyl benzidine, 20 to 2000 $\mu$g and preferably 500 $\mu$g of diphenylamine, 50 to 5000 $\mu$g and preferably 1000 $\mu$g of 4-diphenylamine sulfonic acid, 20 to 1000 $\mu$g and preferably 100 $\mu$g of guaiac, or 2 to 100 $\mu$g and preferably 10 $\mu$g of purified guaiac.

The impregnation with the chromogen can be effected in known manner, for instance by spray or dip techniques.

Impregnation of the support with the said acrylic resins in accordance with the invention results in a considerable improvement in both the sensitivity and the readability of the detection of blood in urine and stool. Thus, for example, the method of the invention extends the limits of the reliable range of detection for hemoglobin in urine, when using o-toluidinium chloride as indicator, from 16–40 mg per liter to 4–8 mg per liter of hemoglobin.

The contours of the color spots which are controlling for the detection are sharper with the procedure of the invention and the overall background shows less coloring.

The substantially slower fading of the color spots as compared with the untreated samples is also favorable for the method. It should be pointed out in particular that the disturbing development of color before the actual "development" is absent so that the zero values remain clearly negative. Furthermore, depending on the individual sensitivity of a chromogen, its quantity, as well as the quantity of polymers, one obtains graded sensitivity and acquires, in particular, a substantially better reliability of the detection of low blood concentrations.

The acrylic resins that are particularly preferred in the method of the invention include those prepared by copolymerization of acrylic or methacrylic acid esters of $C_1$–$C_5$ alcohols, preferably methanol or ethanol, with acrylic or methacrylic acid in weight ratios of 1:4 to 2:1. Mention may be made, in particular, of impregnation of the support with aqueous dispersions of resins prepared by copolymerization of methacrylic acid with ethylacrylate, preferably in a weight ratio of 1:1 is particularly preferred.

COMPARATIVE TESTS

Example 1

The following test papers were prepared with circular filters (diameter=12.5 cm, EDEROL No. 1).

A. Test series with o-toluidinium chloride as indicator.

a. The filters were dipped into an aqueous solution of o-toluidinium chloride (0.1 g/100 ml of distilled $H_2O$) and then dried by hot-air blower.

b. The filters were first treated in the same manner as under a., then dipped into a 3% aqueous dispersion of an ethylacrylate/methylmethacrylate/methacrylic acid copolymer in the approximate ratio of 70:30:1 and also dried by means of a hot air blower.

c. The filters were treated as in part (b) except 3% aqueous dispersion of ethylacrylate/methacrylic acid (in the approximate ratio of 1:1) copolymer was used.

B. Test series with guaiac as indicator.

a'. The filters were dipped into a guaiac solution (0.5 g/100 ml isopropanol) and dried with a hot air blower.

b'. The filters were treated as under Ba', then dipped into an aqueous acrylate copolymer dispersion as described in part Ab and dried with a hot air blower.

C. Application of hemoglobin solutions.

A sample of each filter paper impregnated in accordance with test series A and B was marked with lead pencil in the manner shown in the accompanying drawing.

A stock solution of 4% hemoglobin diluted with distilled water to 0.004% was prepared and applied to positions 2 to 6 on each filter paper to deposit the hemoglobin concentrations indicated immediately below, distilled water containing no hemoglobin being applied to position 1 as a control:

| No. 1 | Blank value: | 50 ul distilled $H_2O$ |
|---|---|---|
| 2 | 1 μl: | 40 ng hemoglobin |
| 3 | 5 μl: | 200 ng hemoglobin |
| 4 | 10 μl: | 400 ng hemoglobin |
| 5 | 20 μl: | 800 ng hemoglobin |
| 6 | 50 μl: | 2000 ng hemoglobin |

D. Development

After complete absorption of the hemoglobin solutions, development was effected with one drop of developer liquid (an alcoholic-aqueous peroxide solution with a 4% peroxide content). At intervals of 30 seconds, 2 minutes, 5 minutes and 15 minutes after application, color photographs were taken.

E. Evaluation of the Results:

Comparison of the photographs of the untreated series Aa and Ba' representing the prior art with the series Ab and Ac on the one hand and with series Bb', prepared in accordance with the application, on the other, greater intensity of color and sharper contours of the corresponding color spots in series Ab, Ac and Bb' were clearly evident.

A more detailed comparison showed that in the untreated series Aa and Ba' conducted with filter paper that was not impregnated with resin the presence of hemoglobin can no longer be evaluated positive at position No. 3, i.e. in concentrations of 200 ng, while in the series Ab and Bb' prepared in accordance with the application there can be not doubt as to the positive result. In the series prepared in accordance with the application even the lowest concentration (position 2) still gives a positive result for the man skilled in the art before the expiration of two minutes.

In the case of filters Aa and Ba', which represent the prior art, clearly positive results can no longer be obtained at all two minutes after development. The situation is entirely different in the case of the Ab, Ac, and Bb' prepared in accordance with the application.

COMPARATIVE TESTS

EXAMPLE 2

An aqueous dispersion of an acrylic resin copolymer comprising 69.2 percent by weight of ethyl acrylate, 29.6 percent of methyl methacrylate, and 1.2 percent of methacrylic acid was prepared.

Next, a series of three solutions was prepared. The first solution contained 100 mg of o-tolidinium chloride dissolved in 10 ml of water and filled to 100 ml with isopropanol. A second solution comprised only the acrylic resin and was prepared by shaking 3.3 ml of a 30 percent aqueous dispersion of the acrylic resin with 96.7 ml of isopropanol. A third solution containing both tolidinium chloride and resin was prepared by combining 10 ml of $H_2O$ containing 100 mg of tolidinium chloride to 90 ml of the just-mentioned solution containing only an acrylic resin. Thus, the third solution simultaneously contained both resin and tolidinium chloride.

These solutions were used to impregnate round filters like those described in Example 1 above. More in particular, a control was prepared by dipping a filter paper into the aforementioned first solution containing only tolidinium chloride. The paper was immediately dried at 50° C. for 15 minutes in a drying oven with the exclusion of light.

Tolidinium chloride and resin were sequentially applied to a second filter paper by first dipping in the aforementioned first solution, drying at 50° C. for 15 minutes in a drying oven with the exclusion of light, and then dipping in the second solution containing resin only. The paper was again dried in the manner discussed above. A third filter paper sample was prepared by dipping in the third solution mentioned above, which contains both resin and tolidinium chloride, i.e. the sample involved simultaneous application of the resin and chromogen. Again, the paper was dried in the manner discussed above.

Human blood, diluted with water to provide a mixture containing 0.004 percent of hemoglobin, was applied to each of the filter paper samples in the form of spots having a diameter from 1 to 5 mm, depending on the amount of solution used. Namely, at a position corresponding to two o'clock on each filter paper, one micro liter of the blood solution was applied. At the four o'clock position, 5 micro liters were applied. At six o'clock, 10 micro liters; at eight o'clock, 20 micro liters; at ten o'clock, 50 micro liters; and at twelve o'clock 50 micro liters of distilled water as a "null value".

Each spot was next developed, including both the null value and the hemoglobulin-containing spots, by the application to the spots of a solution of hydrogen peroxide containing 4 percent of hydrogen peroxide in 70 percent ethanol/$H_2O$. The blue color which developed in the hemoglobin-containing spots was read after 30 seconds and after 2, 5, and 75 minutes.

In each case, those tests involving the filter paper which had been simultaneously impregnated with resin and chromogen gave significantly improved readability and interpretability in contrast to the paper prepared by sequential application of chromogen and resin and in contrast to the control paper comprising only the chromogen. The improved characteristics were the result of a clearer color zone and a better temporal persistence of the color.

COMPARATIVE TESTS

Example 3

An acrylic resin copolymer comprising 50 percent by weight of methacrylic acid and 50 percent by weight of ethyl acrylate, in freeze dried form, is dissolved in pure isopropanol.

Again, solutions containing only tolidinium chloride, only the resin, and a solution containing both tolidinium chloride and the resin were prepared all as in Example 2.

Again following Example 2, filter papers were impregnated with these materials, spotted with a mixture containing 4 percent of hemoglobin, and developed with peroxide.

In all cases, the results were the same as those in Example 2. Namely, the tests employing the filter paper which had been simultaneously impregnated with resin and chromogen were superior in readability and interpretability because of a clearer color zone and a better persistence of the color with the passage of time.

What is claimed is:

1. A diagnostic agent for the rapid detection of blood in excretions and body fluids, which diagnostic agent consists essentially of a filter paper support simultaneously impregnated with
   (1) a chromogenic indicator selected from the group consisting of guaiac and chromogenic phenylamino compounds and capable of color change in the simultaneous presence of peroxidase-active hemoglobin present in blood and of peroxide solution separately applied to said diagnostic agent for development thereof, and
   (2) a resin selected from the group consisting of acrylic resins, methacrylic resins, and combinations thereof, said chromogenic indicator and resin being distributed uniformly or homogeneously throughout said filter paper, and said resin being present in an amount effective to reduce color change reactions prior to development and to promote the persistence of developed color while not interfering with chromatographic transport of the developed reagent.

2. A diagnostic agent as in claim 1 wherein said resin is an anionic acrylic resin, an anionic methacrylic resin, or a combination thereof.

3. A diagnostic agent as in claim 1 wherein said resin is a copolymer of a member selected from the group consisting of acrylic acid and methacrylic acid with a member selected from the group consisting of acrylic acid esters and methacrylic acid esters of $C_1$–$C_3$ alcohols, in a weight ratio from 1:4 to 2:1.

4. A diagnostic agent as in claim 1 wherein said resin is a copolymer of methacrylic acid and ethyl acrylate.

5. A diagnostic agent as in claim 4 wherein said copolymer comprises methacrylic acid and ethyl acrylate in a weight ratio of 1:1.

* * * * *